US010335750B2

(12) United States Patent
Atalla et al.

(10) Patent No.: US 10,335,750 B2
(45) Date of Patent: Jul. 2, 2019

(54) MAGNETIC DRIVE FOR BIOREACTOR

(71) Applicant: GENERAL ELECTRIC COMPANY, Schenectady, NY (US)

(72) Inventors: Ashraf Said Atalla, Clifton Park, NY (US); Klaus Gebauer, Uppsala (SE); Richard Lee Damren, Marlborough, MA (US); David Allan Torrey, Ballston Spa, NY (US); Sima Didari, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 394 days.

(21) Appl. No.: 15/087,656

(22) Filed: Mar. 31, 2016

(65) Prior Publication Data
US 2017/0282137 A1    Oct. 5, 2017

(51) Int. Cl.
*B01F 13/08* (2006.01)
*H02K 5/128* (2006.01)
*H02K 21/24* (2006.01)
*C12M 1/06* (2006.01)

(52) U.S. Cl.
CPC ......... *B01F 13/0827* (2013.01); *C12M 27/02* (2013.01); *H02K 5/1282* (2013.01); *H02K 21/24* (2013.01)

(58) Field of Classification Search
CPC .................................................. B01F 13/0827

USPC ............................... 366/273, 274; 435/302.1
See application file for complete search history.

(56) References Cited

U.S. PATENT DOCUMENTS

| 2,566,743 | A | * | 9/1951 | Okulitch et al. ...... | H02K 49/108 188/264 R |
|---|---|---|---|---|---|
| 3,764,836 | A | * | 10/1973 | Bender ............... | B01F 13/0827 310/103 |
| 6,336,603 | B1 | * | 1/2002 | Karkos, Jr. ............ | A23G 9/045 241/101.2 |
| 2002/0041537 | A1 | * | 4/2002 | Yale .................... | B01F 13/0863 366/273 |
| 2005/0002274 | A1 | * | 1/2005 | Terentiev .............. | B01F 1/0011 366/273 |
| 2006/0092761 | A1 | * | 5/2006 | Terentiev ................ | B01F 7/162 366/274 |
| 2010/0214867 | A1 | * | 8/2010 | Karkos, Jr. ........... | A47J 43/085 366/272 |

* cited by examiner

*Primary Examiner* — David L Sorkin
(74) *Attorney, Agent, or Firm* — Arent Fox LLP

(57) ABSTRACT

The system and method of the invention pertains to use of a back iron on one or both ends of the impeller to increase the magnetic field density, and thus strengthen the magnetic coupling. In addition, pie-shaped (i.e. wedge) magnets, or variations thereof, increase the utilization volume and hence provide higher torque to allow the use of less expensive material (e.g. ferrites). In another embodiment, the rotor side is constructed with a Halbach array which increases the torque without the need to add a back iron piece. In another embodiment, an axial flux stator is implemented to replace the drive-end magnets and the drive motor.

8 Claims, 17 Drawing Sheets

MAGNETIC DRIVE FOR BIOREACTOR

FIELD

Embodiments relate generally to the field of bioreactors, and more particularly to a magnetic drive for a bioreactor.

BACKGROUND

Mixers and pumps have a wide range of applications including bioreactors. The main elements in a mixer 100 (FIG. 1A) are the drive 14 (which contains the driving mechanism) and the impeller 12 (which contains the mixing blades), at the impeller end 11. The two elements are coupled together by different topologies. In one aspect, the magnetic coupling is where the impeller 12 holds a set of magnets 10 that are coupled to the drive end 13. This is established by a set of magnets in the drive end rotated by a separate motor. The existing technology contains a set of cylindrical magnets 14 (See FIG. 1B) on each end separated by a certain "magnetic" gap 16 which is primarily composed of air, fixing elements, and mixing bag wall which are all non-magnetic elements. The existing technology suffers many impediments, including, but not limited to: (1) the weak coupling between the magnets which requires using more expensive and larger magnets (e.g., Neodymium magnets), (2) poor volume utilization, (3) the use of rare-earth magnets in the impeller which is a single use element that increases the cost of the impeller and poses environmental challenges, and (4) large drive size, as it constructs of a set of large coupling magnets driven by a separate electrical motor.

Mixing systems often include an agitator or impeller mechanically connected to a drive shaft lowered into a fluid through an opening in the top of a vessel. The drive shaft is connected to an electric motor arranged outside the vessel. In a closed vessel, a fluid seal is provided between the drive shaft and the wall of the vessel to prevent leakage of fluid from the vessel. Other mixing systems include a rotating magnetic drive head outside of the vessel and a rotating magnetic impeller as an agitation element within the vessel. The movement of the magnetic drive head enables torque transfer and thus rotation of the magnetic impeller allowing the impeller to mix and agitate the fluid within the vessel. Because there is no need in a closed vessel to have a drive shaft penetrate the vessel wall to mechanically rotate the impeller, magnetically coupled systems can eliminate the need for having fluid seals between the drive shaft and the vessel. Magnetic coupling of an impeller inside the vessel to a drive system or motor external to the vessel can eliminate contamination issues, allow for a completely enclosed system, and prevent leakage.

Increasingly, in the biopharmaceutical industry, single use or disposable containers or vessels are used as close type systems, typically in range of about 1-2000 liters. The vessel may be a tank-type support with for example substantially cylindrical shape and is made of rigid material such as stainless steel to provide sufficient support for the flexible bag or container, for example of a kind used in single-use bioreactors. Use of sterilized disposable bags eliminates time consuming steps of cleaning of the vessel and reduces the chance of contamination. The flexible container or bag is placed inside the vessel in an accurate manner so that for example different pipelines or tubes, mixers and sensors can be connected to the bag properly and accurately.

Combining the single use or disposable bags with a magnetic agitator system establishes a sterile environment that is utilized in biopharmaceutical manufacturing. A variety of vessels, devices, components and unit operations for mixing and manipulating liquids and/or for carrying out biochemical and/or biological processes are available. For example, biological materials including mammalian, plant or insect cells and microbial cultures can be processed using bioreactors that include single-use processing bags. Manufacturing of complex biological products such as proteins, monoclonal antibodies, etc. requires, in many instances, multiple processing steps ranging from fermentation or cell culture (bacteria, yeast, insect, fungi, etc.), to primary recovery and purification.

It is desirable to address the needs as stated above by utilizing less expensive elements that are more environmentally friendly. Aspects of the invention will run a much smaller impeller, and have a reduced magnetic force that will allow the bag to be separated from the drive more easily. Further, moving parts on the drive (user) end will be addressed to provide safer mechanisms.

SUMMARY

The system and method of the invention pertains to a magnetic drive for a bioreactor mixer or pump that strengthens the magnetic coupling to provide higher torque and replace the drive-end magnets and drive motor. Embodiments disclosed herein use a back iron on both ends to strengthen the magnetic coupling as well as a pie-shaped magnets ("pie" shaped in the sense of a wedge shape and format (i.e., triangular/trapezoidal have a wider outer edge and smaller inner dimension) to increase the volume utilization and hence provide higher torque and allow the use of less expensive material (e.g. ferrites). In another embodiment, the rotor side is constructed with a Halbach array which increases the torque without the need to add a back iron piece. Another embodiment implements an axial flux stator to replace the drive-end magnets and the drive motor.

One embodiment of a system is utilized as bioreactor mixer, the system comprising: a rotating drive, a fixed shaft, an impeller capable of rotating around the fixed shaft, a plurality of magnets positioned in one or more array formats, a first set of magnets in a first array format positioned at a drive end adjacent the rotating drive and a second set of magnets in a second array format positioned at the impeller, and at least one plate including the first set of magnets positioned thereon such that the first set of magnets are positioned in a concentric geometric configuration and individually shaped with a wider outside dimension that narrows toward a center of the concentric geometric configuration; wherein the second set of magnets are arranged adjacent one another to augment a magnetic field on one side of the second array while cancelling the magnetic field to zero on an opposite side of the second array to achieve a spatially rotating pattern of magnetization. In one aspect, the system further comprises an external vessel into which at least a portion of the bioreactor mixer is placed.

In another embodiment, a system is utilized as bioreactor mixer, the system comprising: a rotating drive, a fixed shaft, an impeller capable of rotating around the fixed shaft, a plurality of magnets positioned in one or more array formats, a first set of magnets in a first array format positioned at a drive end adjacent the rotating drive and a second set of magnets in a second array format positioned at the impeller, and at least a first plate including the first set of magnets positioned thereon; wherein the second set of magnets are positioned with a second plate comprising a material having magnetic permeability greater than the magnetic permeability of air and sandwiched between the first set of magnets and the impeller, such that a magnetic field gradient is created between the first array format of the first set of magnets and the second array format of the second set of magnets.

In one aspect, the first plate comprises a material having magnetic permeability greater than the magnetic permeability of air. The first set of magnets can be positioned in an array format geometrically shaped with a wider outside dimension that narrows toward a concentric center. The second set of magnets can be positioned in an array format geometrically shaped with a wider outside dimension that narrows toward a concentric center.

Detailed descriptions of various embodiments are described as follows.

DETAILED DESCRIPTION

Figure 1A:
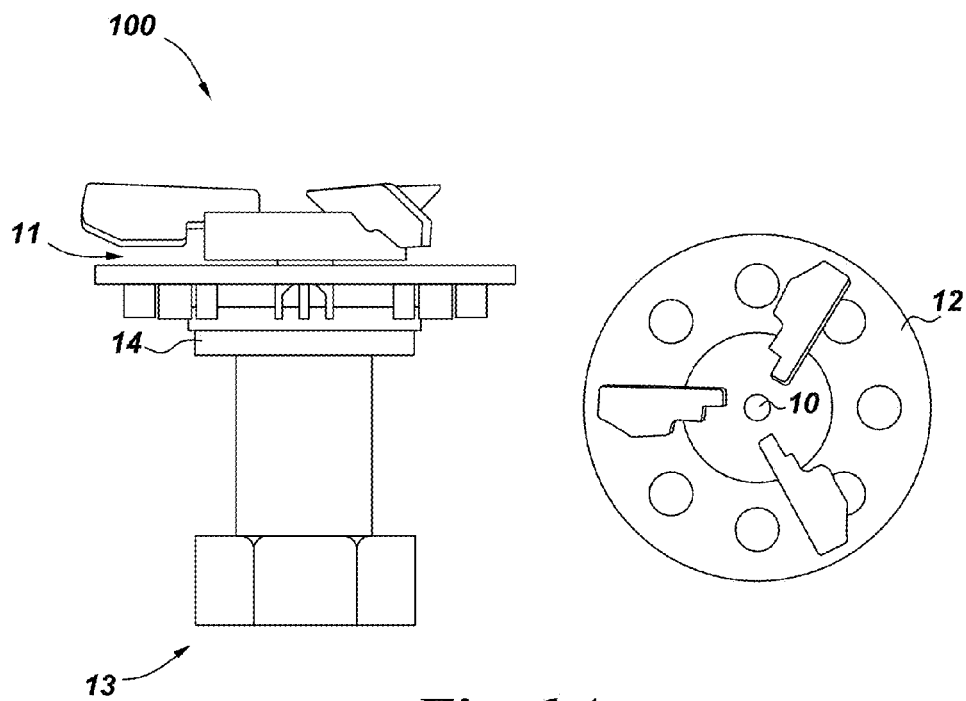
FIG. 1A (PRIOR ART) illustrates the magnetic drive for a bioreactor mixer.
Figure 1B:
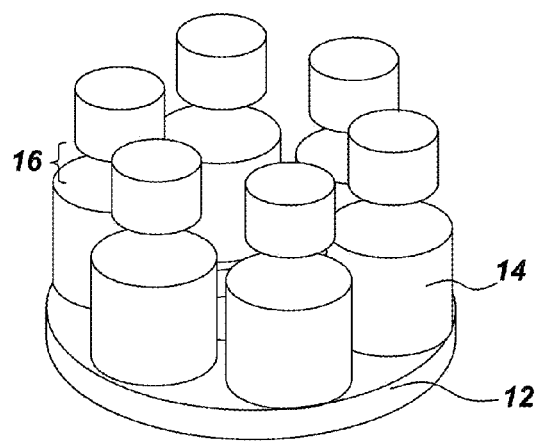
FIG. 1B (PRIOR ART) illustrates a magnetic coupling where the impeller holds a set of magnets that are coupled to the drive end, the set of magnets in the drive end rotated by a separate motor.

Various embodiments will be better understood when read in conjunction with the appended drawings. It should be understood that the various embodiments are not limited to the arrangements and instrumentality shown in the drawings.

The system and method of the embodiments disclosed pertain to a magnetic drive for a bioreactor mixer or pump that strengthens the magnetic coupling to provide higher torque and replace the drive-end magnets and/or drive motor, as desired. Embodiments include magnetic shapes and arrangements as well, including pie-shaped magnets ("pie" shaped in the sense of a wedge shape and wedged format (i.e., triangular/trapezoidal have a wider outer edge and smaller inner dimension), such that the wedges fit together to increase the volume utilization and hence provide higher torque, and further allow the use of less expensive material (e.g. ferrites). In one embodiment, the rotor side is constructed with a Halbach array which increases the torque. Embodiments disclosed may utilize a back iron on one or both ends to strengthen the magnetic coupling. With the Halbach array, torque is increased without a back iron piece. Another embodiment implements an axial flux stator to replace the drive-end magnets and the drive motor. Embodiments are disclosed as follows.

Pie-Shaped Magnet Configuration

Figure 2:
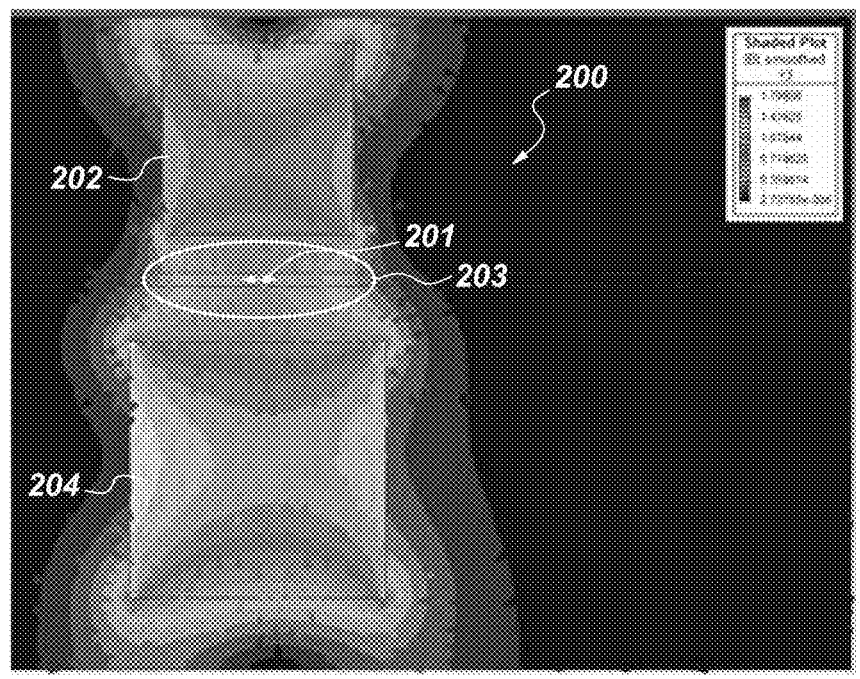
FIG. 2 (PRIOR ART) depicts a cross-sectional view of the magnetic field coupling in a prior art system.
Figure 3:
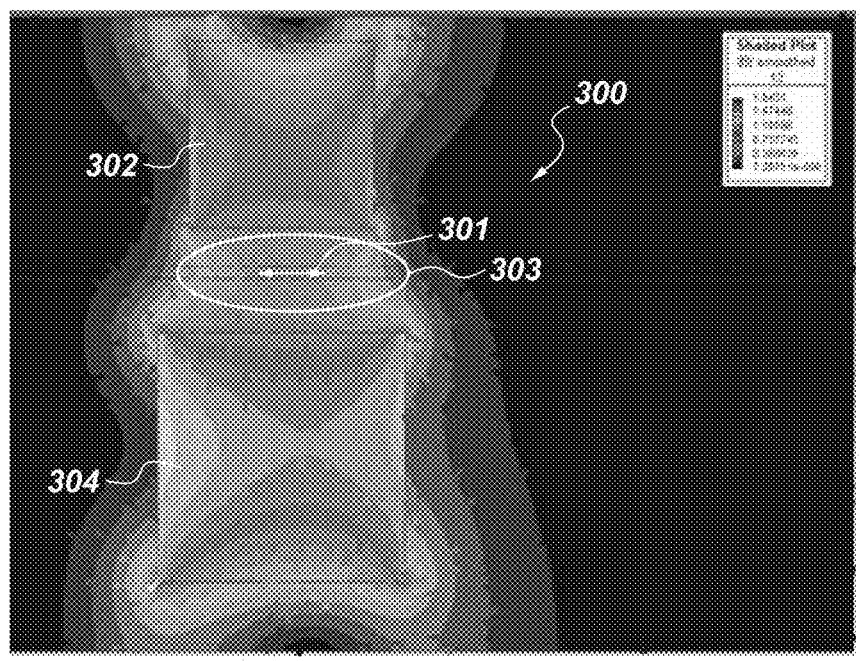
FIG. 3 depicts a cross-sectional view of the magnetic field coupling when using the individual magnet shapes and configuration as disclosed in embodiments herein.

For comparison purposes, FIG. 2 depicts a cross-sectional view of the magnetic field coupling 201 in a prior art system between a drive end magnet 202 and an impeller end magnet 204; The magnetic field density 203 is the area represented there between. An embodiment disclosed herein is shown in FIG. 3 where pie-shaped magnets are utilized in the mixer 300. A cross-sectional view shows a large increase in the magnetic field coupling 301, the increased magnetic field density 303 between the drive end magnet 302 and impeller end magnet 304.

Figure 4A:
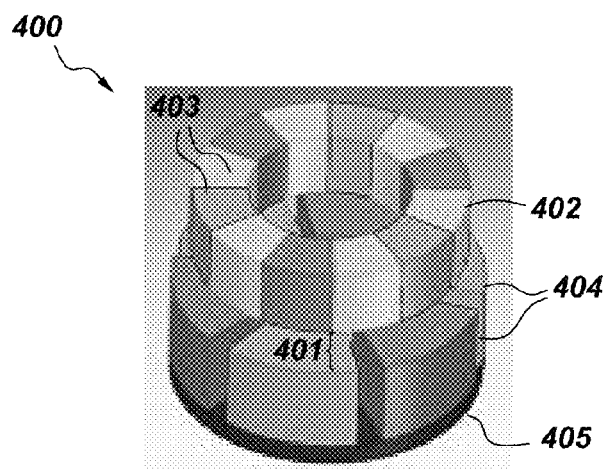
FIG. 4A illustrates the rotor side constructed with a Halbach array in another embodiment, the individual magnets adjacent one another without spacing to form a concentric magnetic arrangement.

FIG. 4A depicts the rotor side of a mixer 400 with a Halbach array 402 in one embodiment. The individual magnets 403 are adjacent one another without spacing to form a concentric magnetic arrangement of the Halbach array 402. The pie-shaped impeller end magnets 404 are spaced apart and positioned on a magnetic plate 405. The magnetic plate may be a back iron, any magnetic material, including but not limited to any material of magnetic permeability greater than air. In one aspect, the magnetic plate may be a high magnetic permeability allow such as cobalt, iron, or other magnetic material. A magnetic field density 401 is created by the space remaining where the individual magnets 403 of the Halback array 402 levitate above the impeller end magnets 404.

Back Iron at Impeller and Drive Ends

Figure 4B:
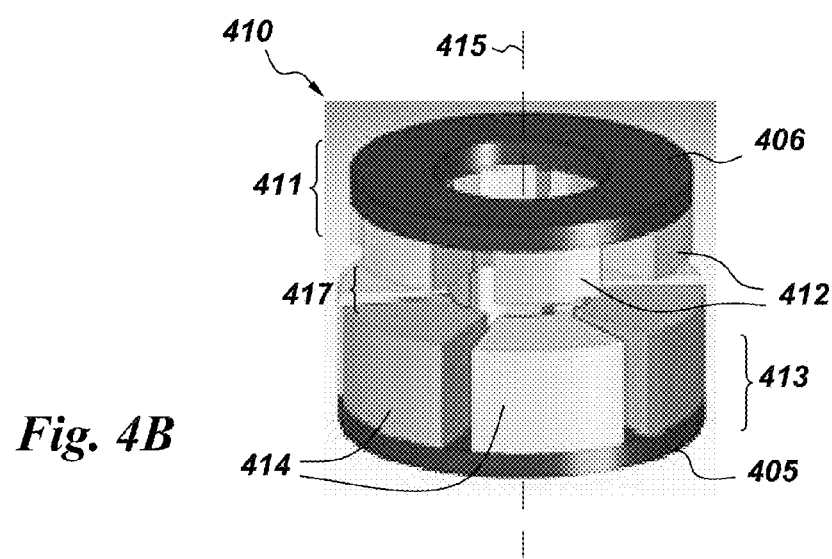
FIG. 4B illustrates an embodiment including pie-shaped magnets, individually positioned, angled, and spaced in a magnetic arrangement around a central axis.

FIG. 4B illustrates an embodiment of a magnetic drive 410 including wedged (pie-shaped) magnets 412 at a drive end 411 and wedged (pie-shaped) magnets 414 at an impeller end 413, each magnet 412, 414 individually positioned, angled, and spaced in a magnetic arrangement around a central axis 415. A magnetic plate 405 is positioned at the impeller end 413 while a second magnetic plate 406 is positioned at the drive end 411. The magnetic plates 405,

406 are a back iron, in one embodiment, and may be any magnetic material, including but not limited to any material of magnetic permeability greater than air. A magnetic field density 417 is created between the drive end magnets 412 and impeller end magnets 414, thus increasing the magnetic coupling. In another aspect, the magnetic plate is a high magnetic permeability including materials including, but not limited to, cobalt, iron, or other magnetic material.

Figure 4C:
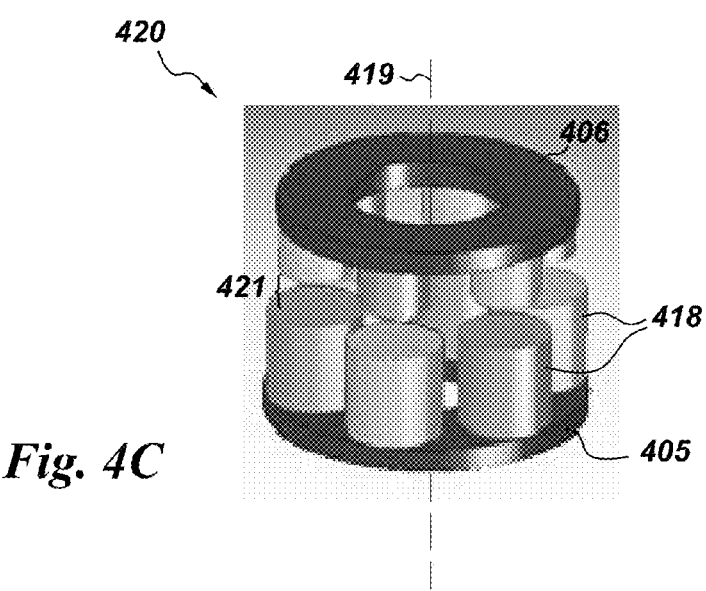
FIG. 4C illustrates an embodiment of the invention including a back iron on both ends.

In one embodiment, as shown in FIG. 4C, a magnetic drive 420 includes an impeller end back iron 405 and drive end back iron 406. The cylindrical shaped magnets 418 are spaced around a central axis 419, and positioned at each end such that a magnetic field density 421 is created therebetween. The back irons enhance the magnetic coupling of the magnetic drive, thereby increasing torque.

As illustrated in FIG. 4C, back iron is placed in the shape of the impeller above the drive end magnets and below the impeller end magnets. The back iron reduces the overall magnetic path in air, the magnetic field density 421, between the drive end and the impeller end magnets. As a result, the magnetic field density that couples the two ends increases.

Figure 5:
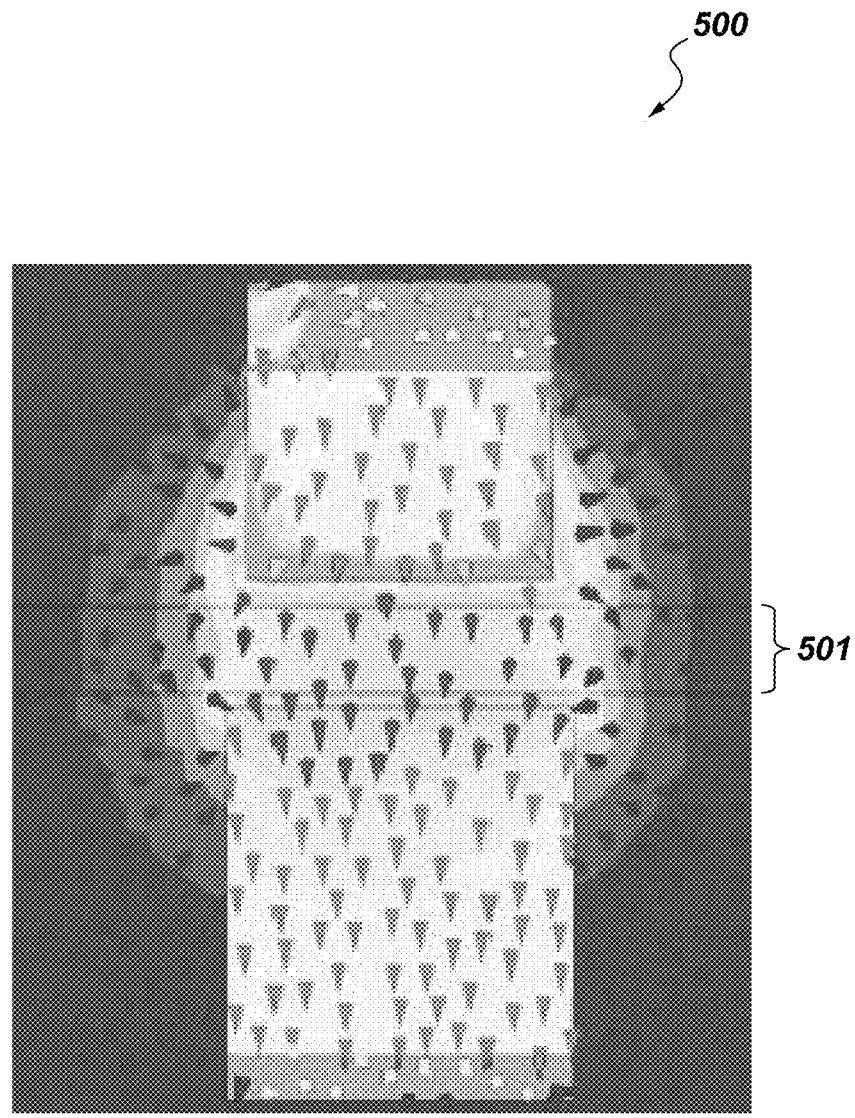
FIG. 5 depicts a cross-sectional view showing the magnetic coupling in embodiments disclosed herein when using the pie-shaped magnets and back iron.

FIG. 5 depicts a cross-sectional view of a mixing system 500 showing the magnetic coupling 501 in embodiments disclosed herein when using the pie-shaped magnets and back irons, as described in FIG. 4B.

Figure 6:
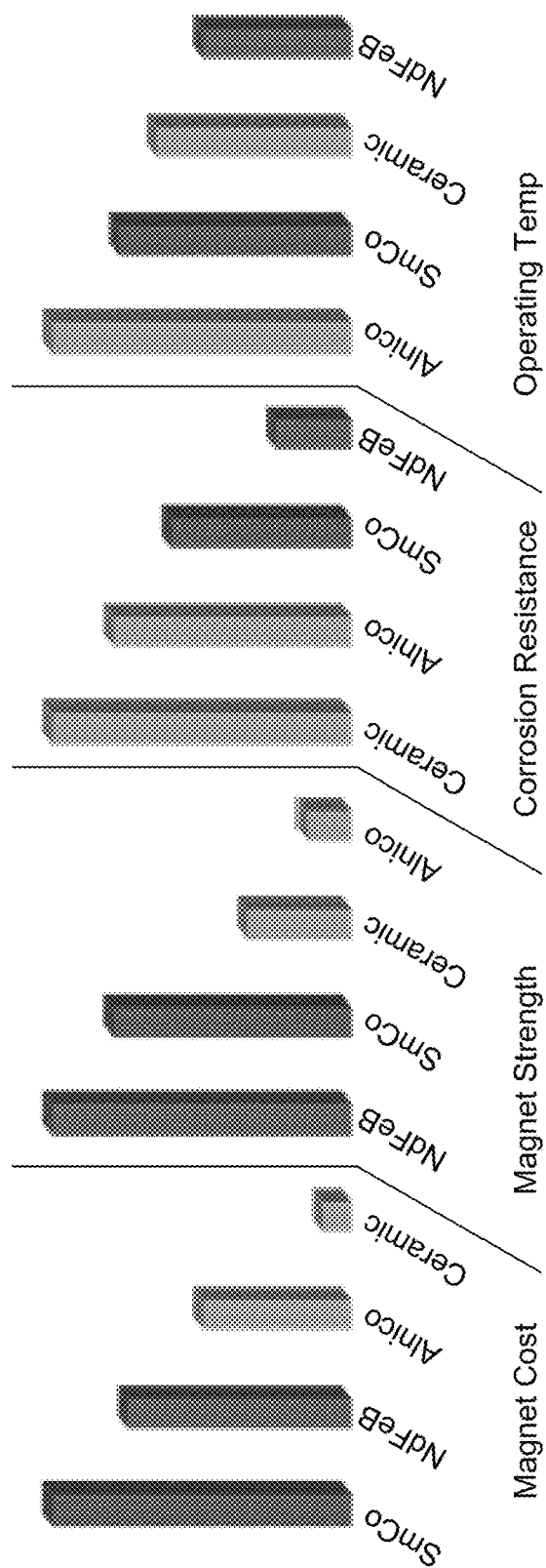
FIG. 6 provides a comparison of magnets as utilized in embodiments of the invention.

A comparison of magnets is shown in FIG. 6. Baseline torque is at about 5.8 Nm with cylindrical shaped magnets as shown in FIG. 4C. Note that . . .

TABLE 1

Materials used for the magnets in the magnetic drive.

| Material | | Grade | Magnet price ($/kg) |
|---|---|---|---|
| Rare Earth | Sintered NdFeB | N42SH | 70 |
| | SmCo | 28/7 | 87 |
| Non-rare Earth | Alnico | Alnico 9 | 57 |
| | Ferrite | C8B/AC12 | 8.5 |

Table 1: Materials used for the magnets in the magnetic drive.

FIG. 6 illustrates that the cost of non-rare earth materials, e.g., Alnico 9 and C8B/AC12 (ceramic) are cheaper and have beneficial characteristics that align with the desired magnetic compositions, characteristics, and configurations described.

Figure 7:
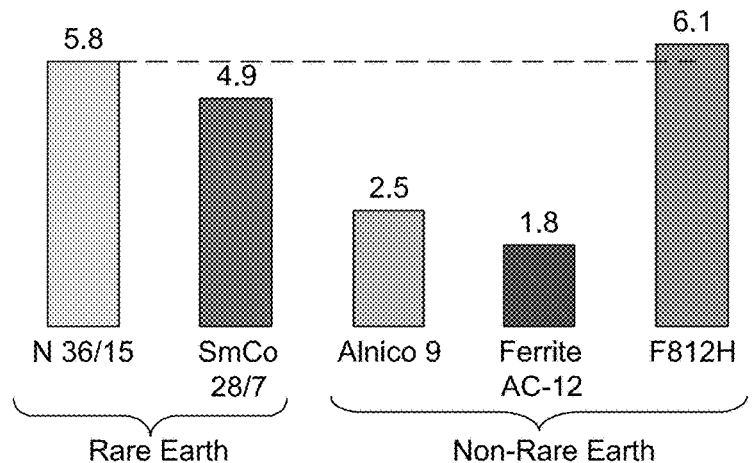
FIG. 7 depicts a comparison of maximum torque for cylindrical magnets using different materials in one embodiment.

FIG. 7 is a comparison of maximum torque for cylindrical magnets ($\phi=0.75 \times 0.75$). By replacing Neodymium (Sintered NdFeB) magnets, and using other non-rare earth magnets, while keeping the cylindrical shapes and arrangement, the torque production is greatly reduced.

Figure 8:
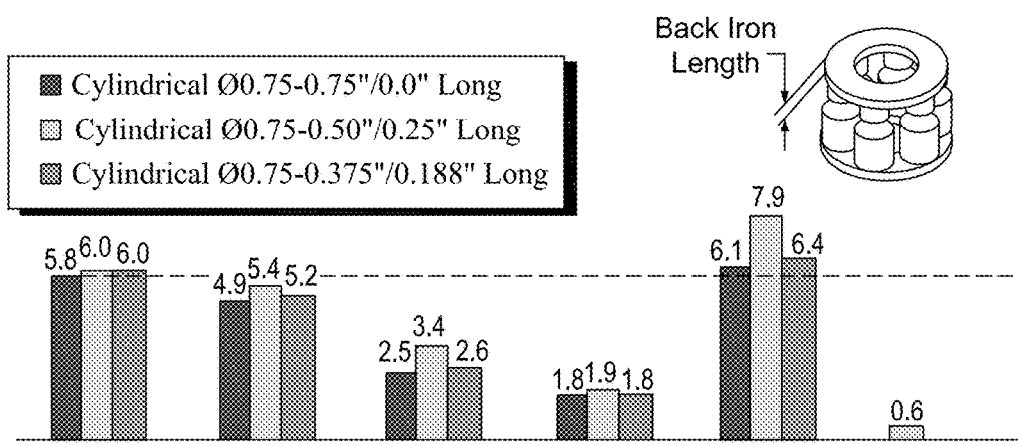
FIG. 8 depicts a comparison of maximum torque for cylindrical magnets with back iron.

In another aspect, back iron may be added on one of the impeller end or the drive end. Back iron added at impeller and drive ends improves torque production, as illustrated in FIG. 8. Specifically, FIG. 8 demonstrates the comparison of maximum torque for cylindrical magnets with back iron, as represented in FIG. 4C. FIG. 8 shows that maximum torque produced by different types of magnets (e.g., N 38/15, SmCo 28/7, etc.) as a function of magnet geometry. The ferrite magnet grade FB12H gives twice the amount of the torque produced without the back plate, while eliminating the use of rare earth magnets. Three of the magnet grades are not able to produce the baseline torque of the rare earth magnets.

Figure 9:
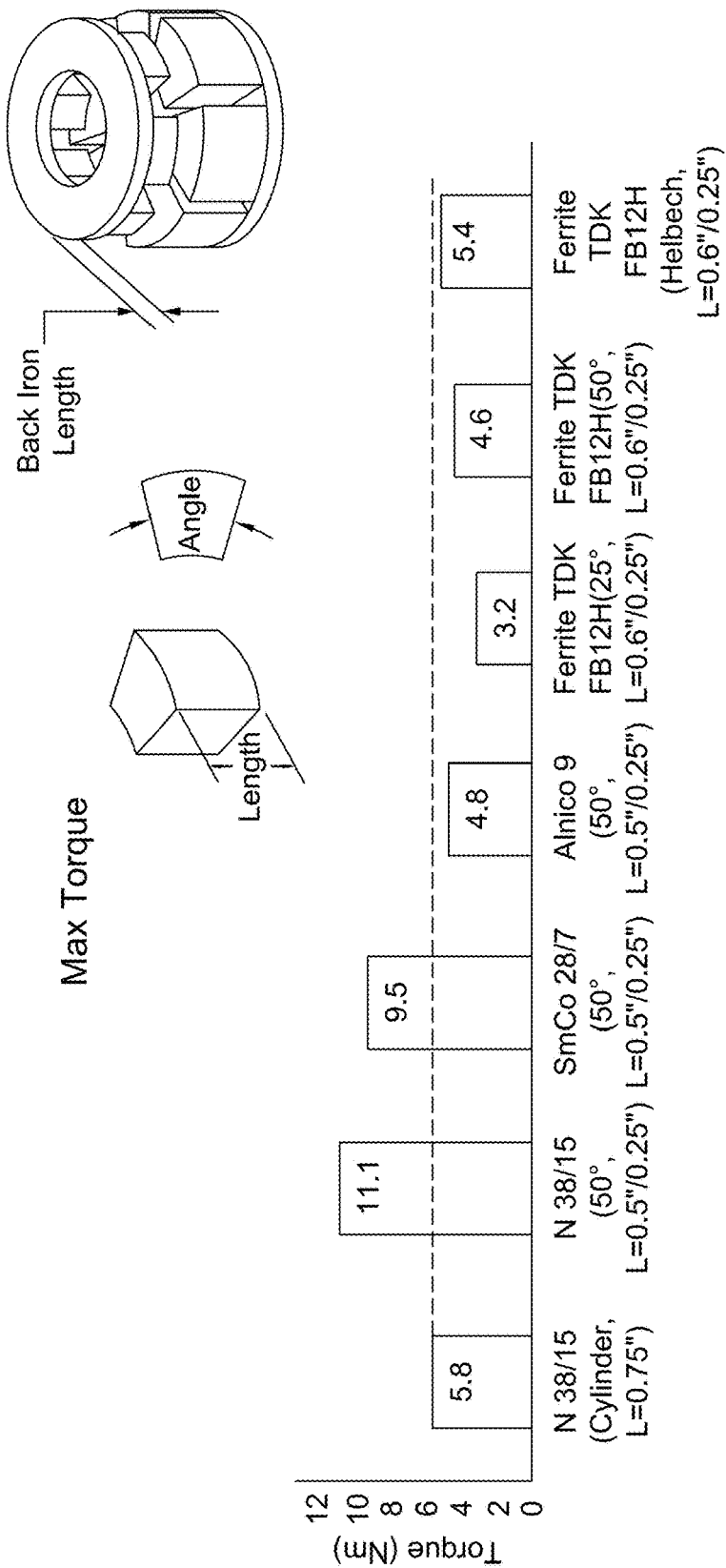
FIG. 9 depicts a comparison of maximum torque for pie-shaped magnets and Halbach array

Embodiments of the invention modify the shape of the magnets from cylindrical to pie-shaped configurations. As shown in FIG. 9, the improved impeller-drive design provides 2.5 times the torque without the need for expensive Neodymium magnets. Ferrite magnet grade FB12H gives 2.5 times the amount of torque produced without the back plate and the magnet pie shape. As demonstrated in FIG. 4B, and referenced in FIG. 9, a comparison is shown of maximum torque for pie-shaped magnets.

Halbach Magnet Array

As shown in FIG. 9, an embodiment of the Halbach impeller-drive design of FIG. 4A provides the desired torque without the need for expensive Neodymium magnets. This arrangement of Halbach array and pie shaped increases the torque produced by a factor of 3 which delivers the baseline torque.

Axial Flux Stator

Figure 11:
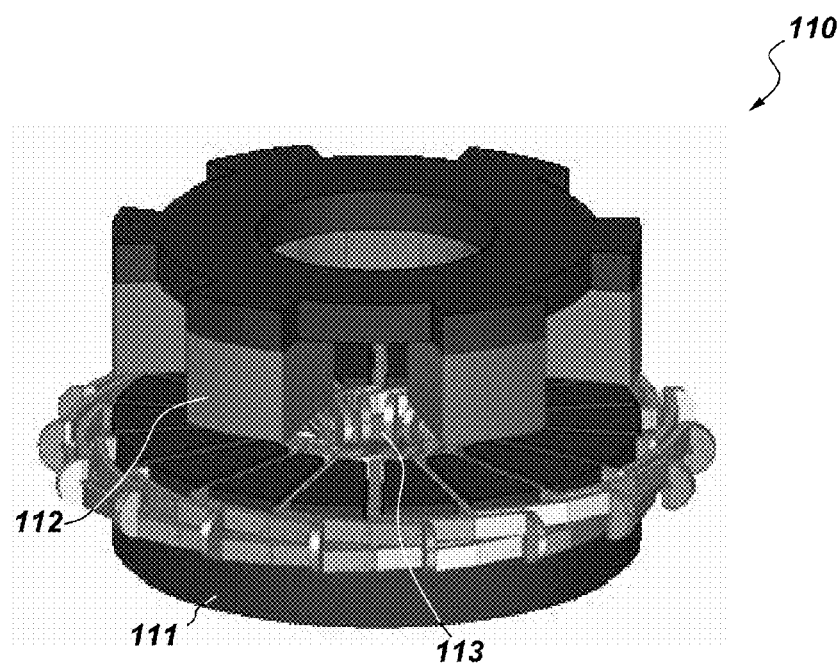
FIG. 11 illustrates an embodiment of the invention from a perspective side view.

Embodiments of the invention provide an axial flux stator to reduce the drive end size, as well as reducing the number of components, and increase its reliability. FIG. 11 depicts an embodiment of the axial flux stator 110 without the shaft and bearing, and without the lever mechanism as utilized in the prior art. The drive stator 111 is positioned on an underside of the magnets 112 and has a control circuit 113.

The electrical and mechanical components of the axial flux stator 110 are adjusted to address challenges in the modified design. In embodiments of the axial flux stator, the electrical components comprise: high current density (cooling), a higher number of slots to allow high count of slots per pole and hence the ability to choose various coil span (to suppress harmonics), longer slots resulting in higher leakage inductance and lower power factor, and higher current results in higher flux thus accommodating a bigger tooth to avoid saturation.

Figure 12:
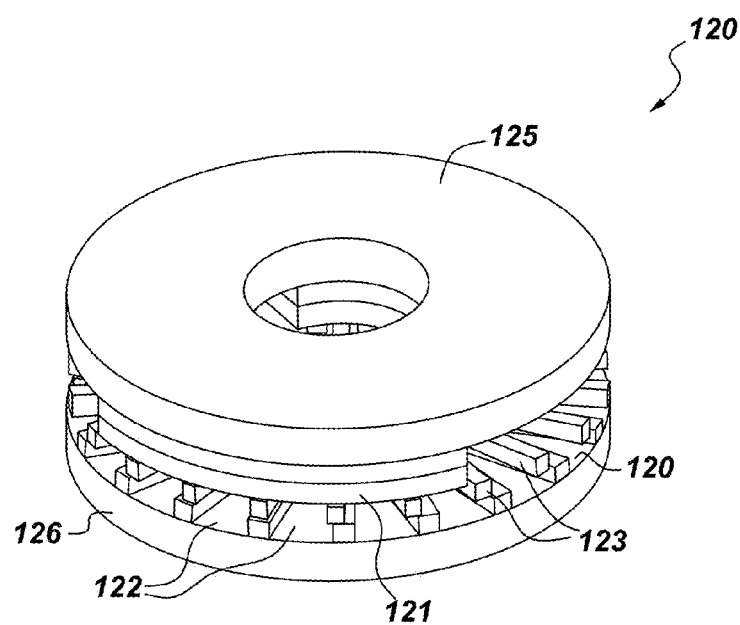
FIG. 12 illustrates an embodiment of the invention from a perspective side view.

The construction of the axial flux stator 120 is depicted in FIG. 12 as an axial-type magnetic gear. A magnetic core 121 is positioned between a high speed rotor 125 (stator with high frequency) and a low speed rotor 126. The magnetic core 121 has a number of slots 122 depending on the arrangement of the impeller magnets and windings. The magnetic core may be laminated, powder type, or a taped core, as desired. A set of windings are shown in FIG. 12 as stationary steel segments 123, or stator teeth, with modulation slots 122. The set of windings may be tooth-wound, distributed, or fractional windings, as well. Windings can also be single or multi-layer, wave or lap windings, full or short pitched windings. The stationary steel segments can have additional slotting to accommodate magnetic gearing (e.g., Vernier type machine) with single or multi-stage gearing. The stator can also have additional magnets when using a Vernier type machine.

Figure 13A:
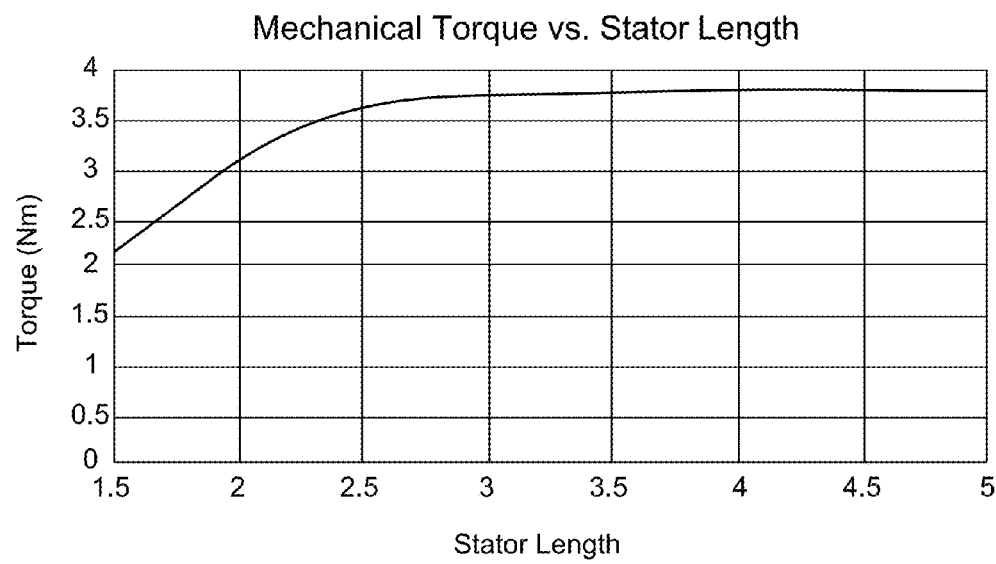
FIG. 13 (a), (b), (c) shows analyses of varying the stator length.
Figure 13B:
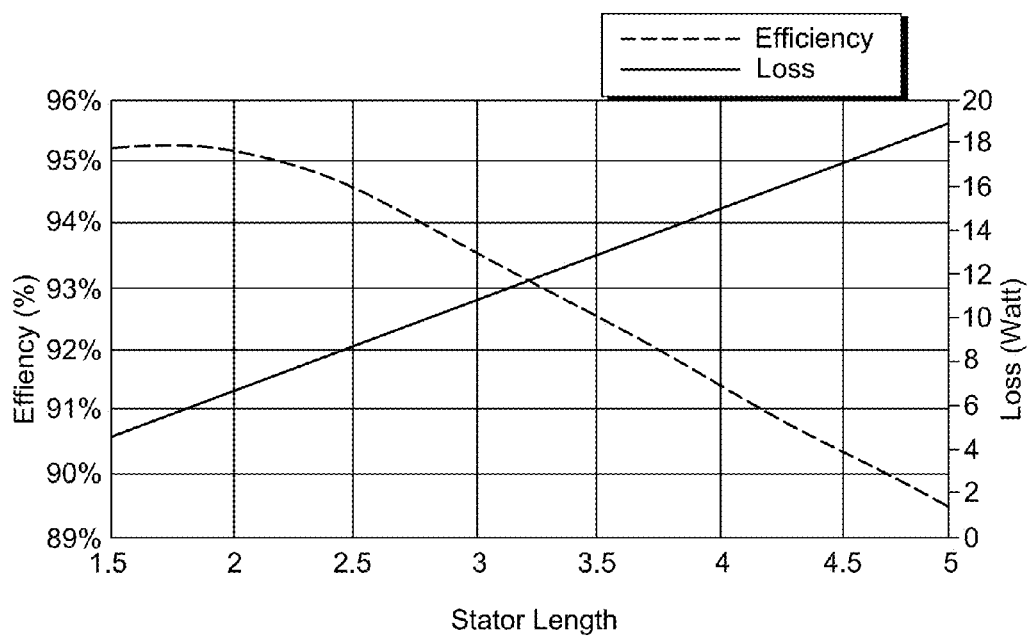
Figure 13C:
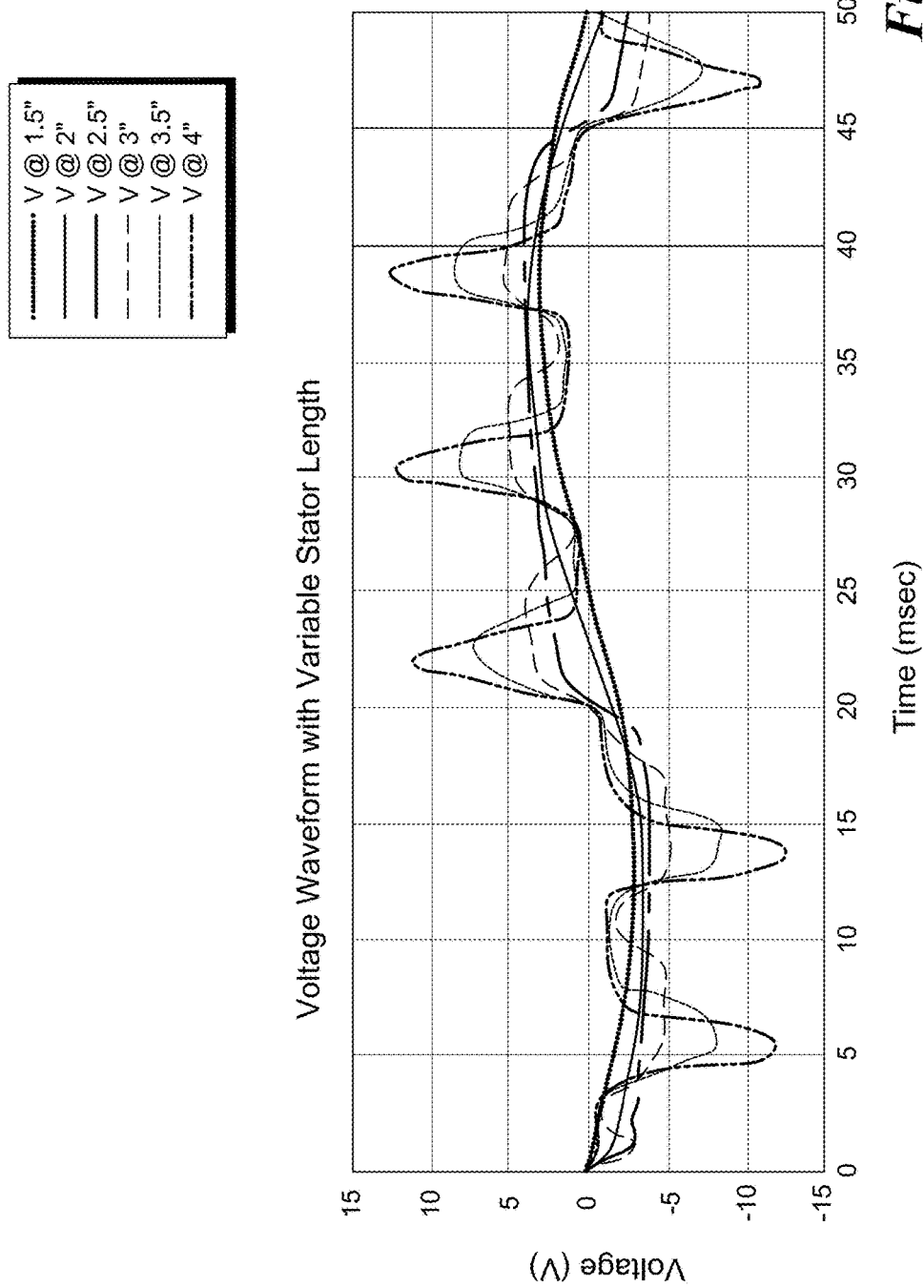
Figure 14A:
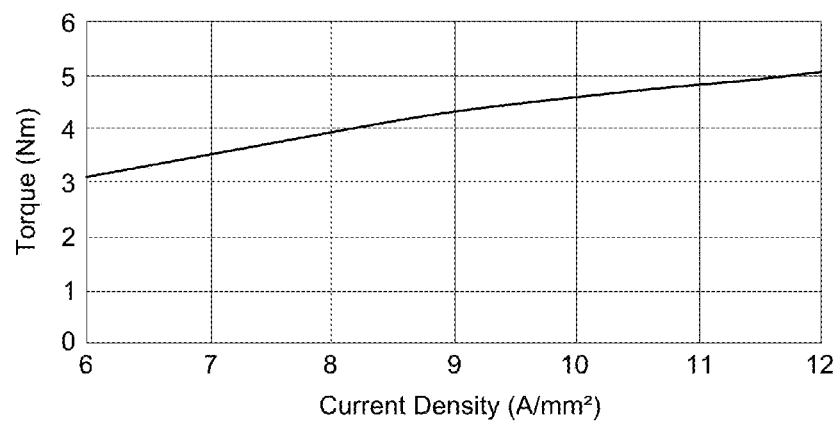
FIG. 14 (a), (b), (c) shows an analyses of varying the current density.
Figure 14B:
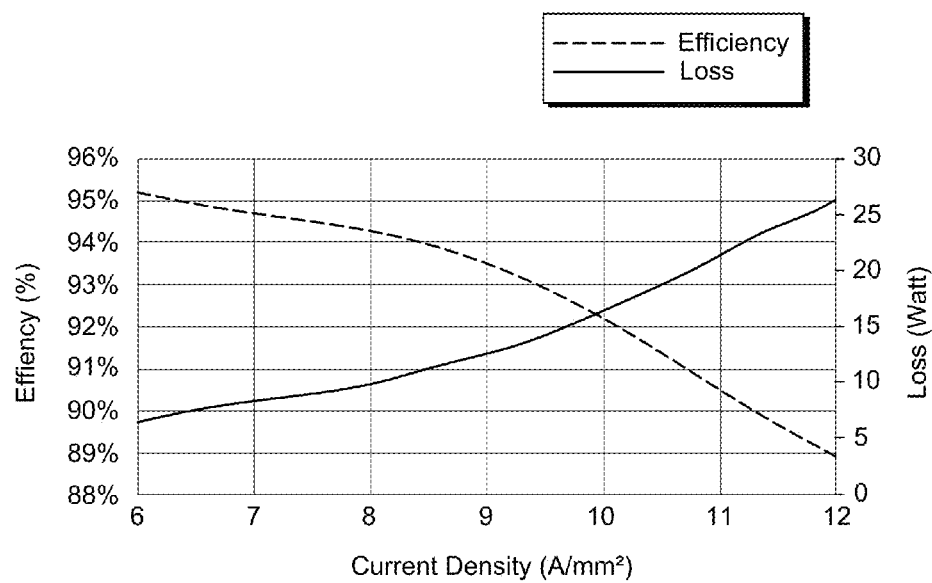
Figure 14C:
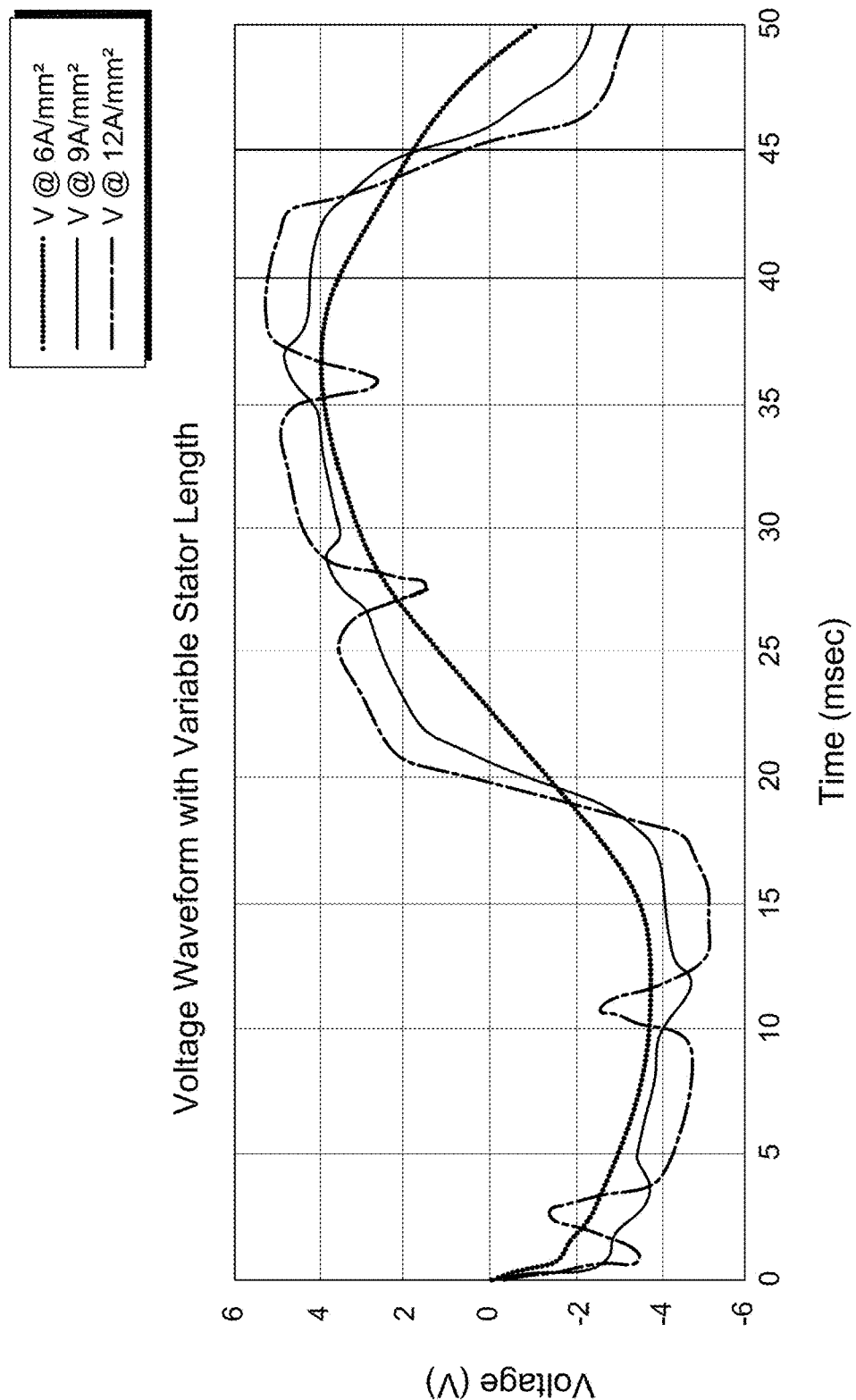
Figure 15A:
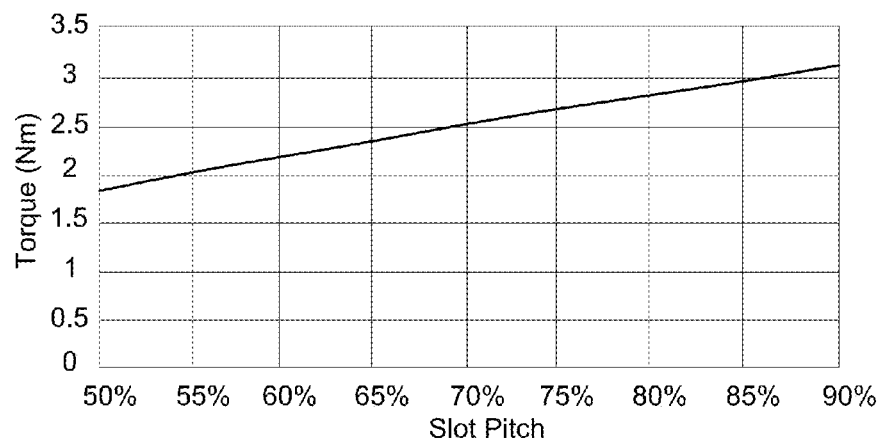
FIG. 15 (a), (b), (c) demonstrates analyses of varying the slot pitch, and resulting torque.
Figure 15B:
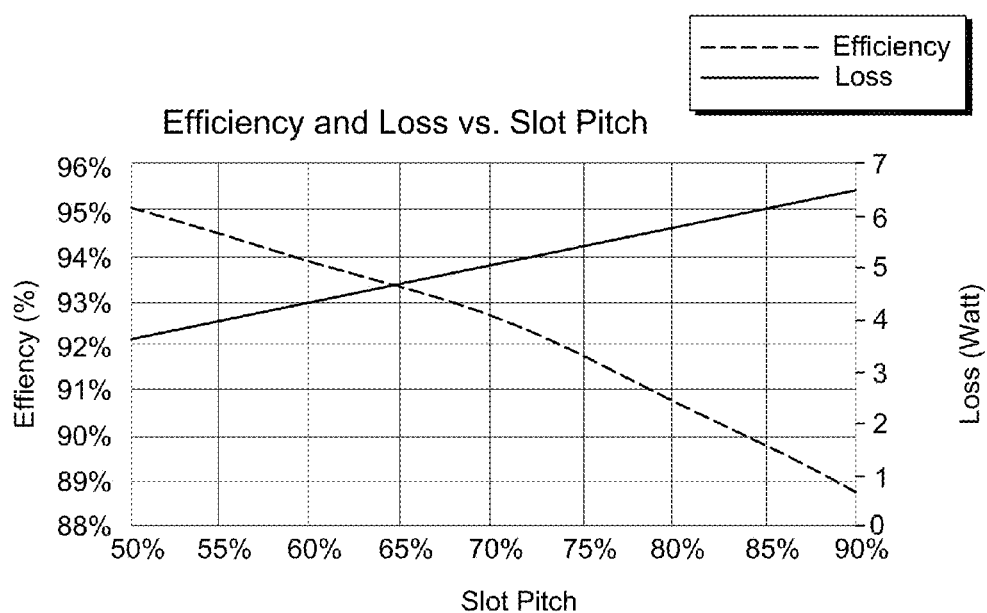
Figure 15C:
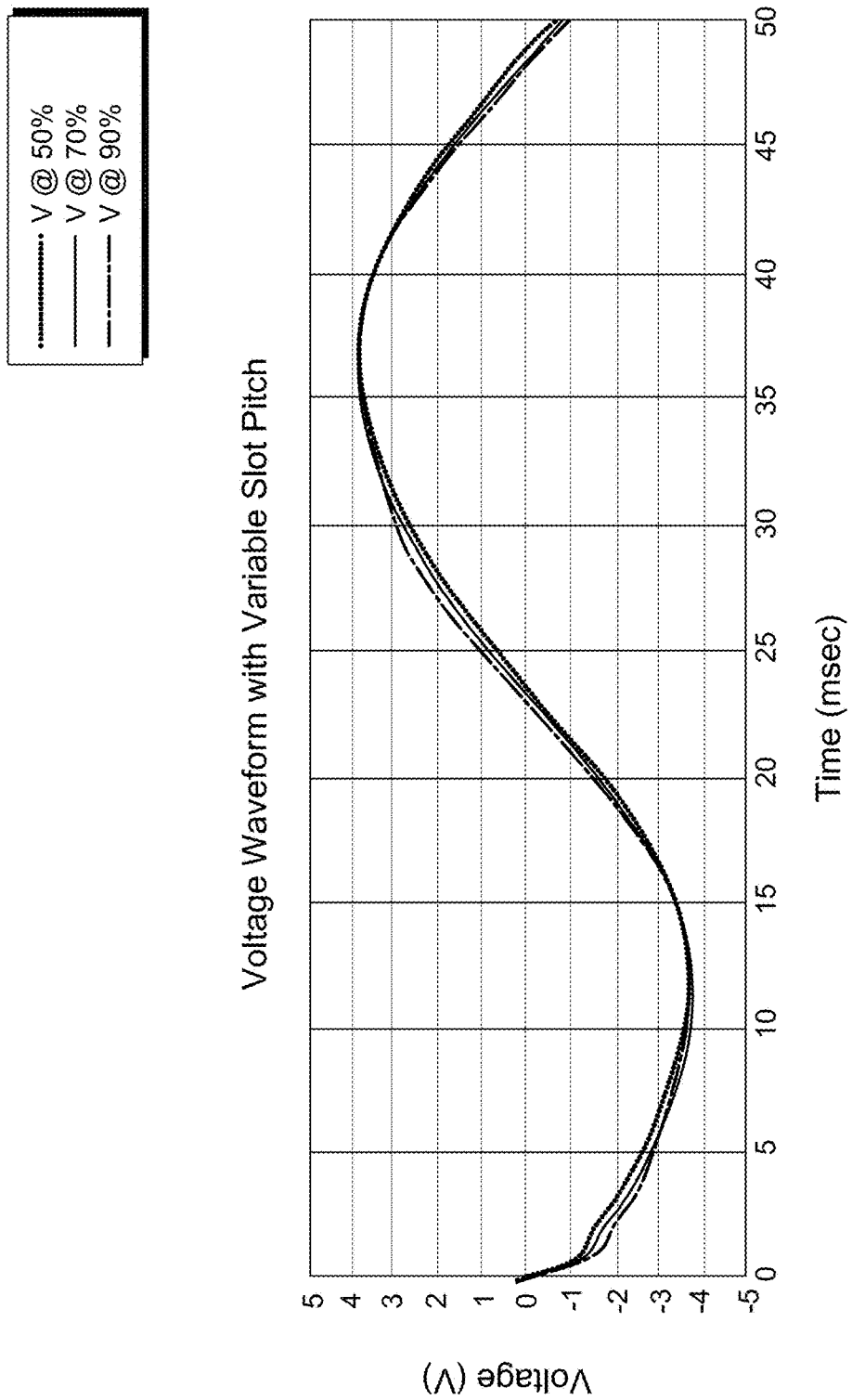

An analysis of the axial flux stator with distributed windings (e.g., an 18 slot example) demonstrates that by increasing the stator length, a higher current path results per slot; saturation of the teeth occurs and causes increased harmonics (See FIG. 13). Increasing the stator current density results in higher torque; again, saturation of the teeth occurs and causes increased harmonics (See FIG. 14). And, by increasing the stator slot pitch, higher torque results while placing mechanical constraints on the innermost tooth width (See FIG. 15).

Figure 16A:
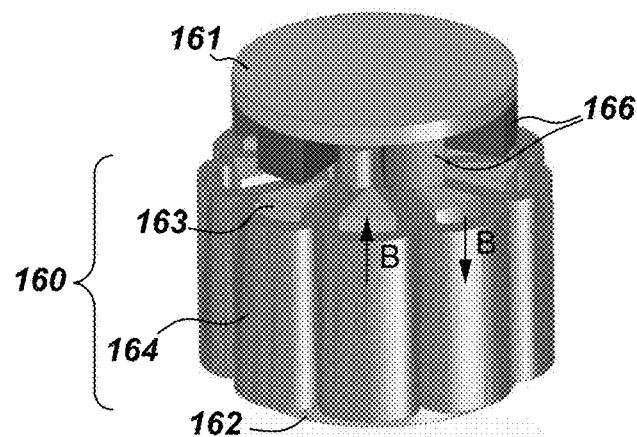
FIG. 16A illustrates a perspective view of an embodiment of a tooth wound axial flux stator.
Figure 16B:
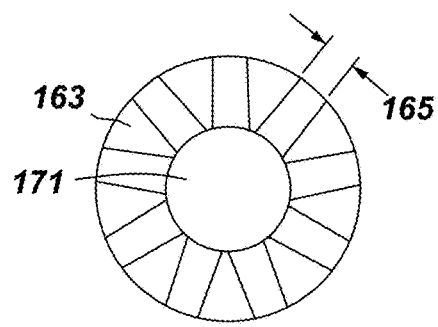
FIG. 16B depicts a perspective top view of the axial flux stator of FIG. 16A.
Figure 16D:
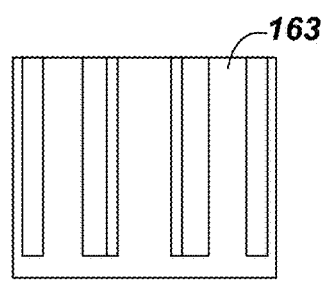
FIG. 16D depicts a perspective side view of the tooth height of the axial flux stator of FIG. 16A.
Figure 16C:
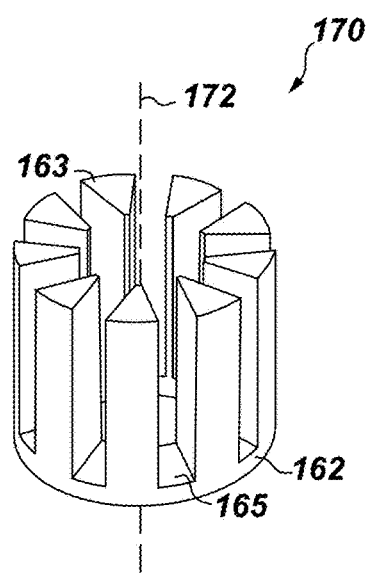
FIG. 16C depicts a perspective side view of the axial flux stator of FIG. 16A.

FIG. 16A illustrates an embodiment of a tooth wound axial flux stator 160 with nine (9) slots 165 (See FIG. 16C), for exemplary purposes, and not limitation. FIGS. 16B, 16C, and 16D depict perspective views to more clearly illustrate the details of the axial flux stator 160. The stator core comprises pie-shaped magnetic stator teeth 163 that extend vertically from the stator back iron 162. The stator core 170 can be formed from sintered powdered iron, ferrite, or machined from a coil of magnetic steel. Conductive windings 164 are wound around the stator teeth 163. The conductive windings are divided up into phases. Within each phase winding, the sense, field direction, of the individual coils alternates so that the application of phase current to the phase winding creates a magnetic field that is directed vertically upward in one tooth and vertically downward in another tooth. The flow of current through the conductive windings forms a magnetic field that flows through the stator teeth, across the air gap between the stator 160 and a rotor 161, interacts with the magnets 166 on the rotor, travels through the rotor 161, and returns through a rotor magnet of opposite magnetic polarity, across the air gap between the stator and rotor, through an oppositely-excited stator tooth, closing through the stator back iron 162.

As shown in FIG. 16B, the exemplary stator has nine slots 165 of width of about 0.470 in; the inside diameter (a hollow core 171 with central axis 172) of the stator core 170 is about 1.575 in, and the outside diameter of the stator core is about 3.250 in. The width of the slots, the core inside diameter, and core outside diameter are parameters that determine the performance of the motor. FIG. 16C depicts the magnetic stator core 170 including stator teeth 163 in combination with the base back iron 162 and shows that the stator core is about 2.750 in height, but can vary in size, shape and dimension, as desired for a particular mixer. FIG. 16D depicts the height of the magnetic pie-shaped stator teeth 163, the height of which is shown here as about 2.500 in. The height of the stator teeth and the thickness of the stator back iron are additional parameters determined during the design of the motor, and so may be varied in shape and dimension.

Figure 16E:
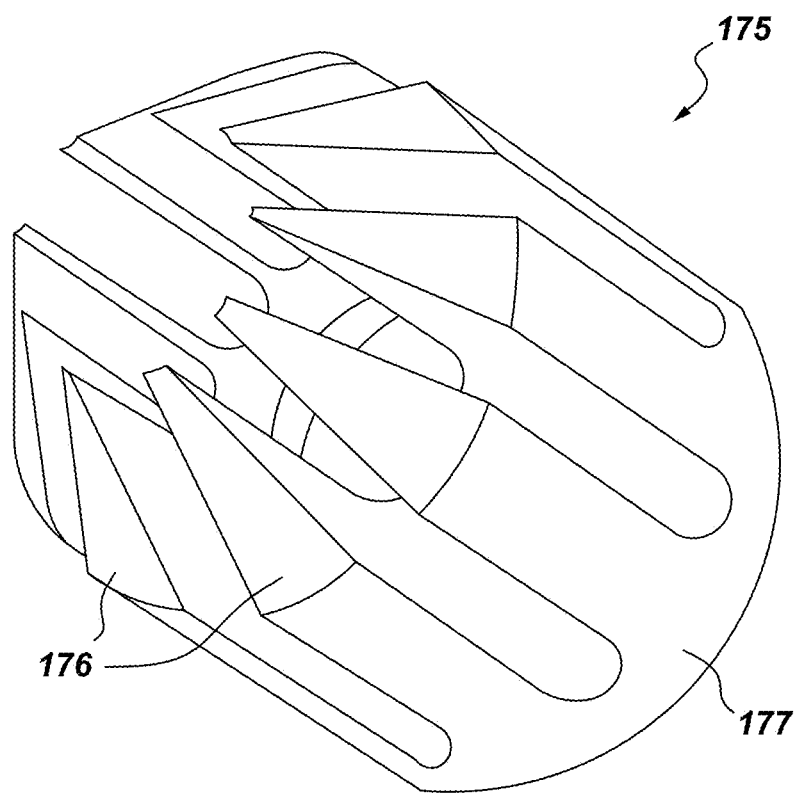
FIG. 16 E depicts an embodiment of a stator core described herein.

In another embodiment, as shown in FIG. 16E, the stator core 175 is defined with conic teeth 176 and including a back iron 177. As such, the stator core may be modified and designed to provide operational efficiency of a mixer.

Figure 10:
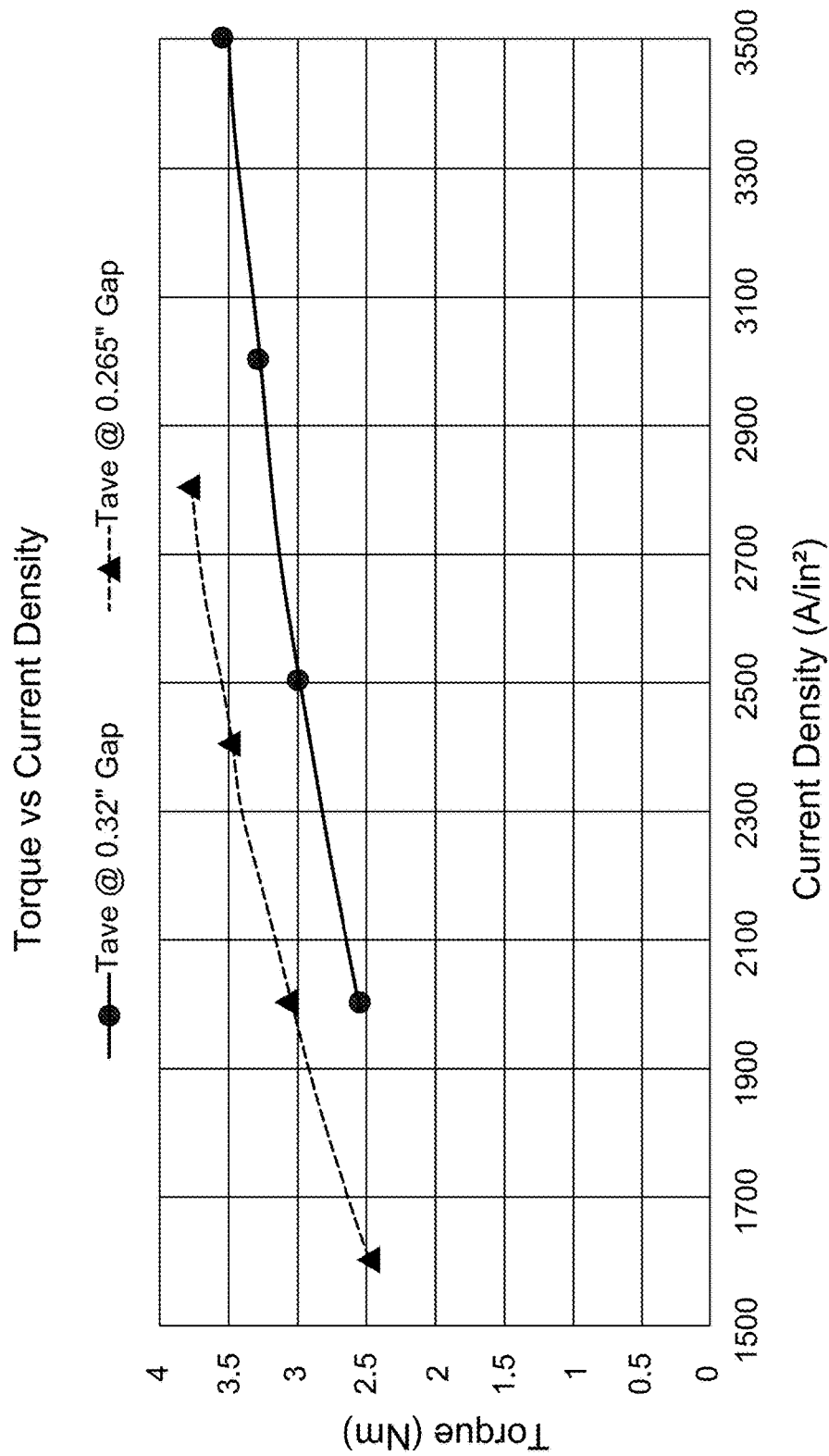
FIG. 10 depicts a graphic illustration of the relationship of torque versus current density for the axial flux stator in one embodiment.

FIG. 10 compares torque versus current density of the axial flux stator 160 for gaps of about 0.32 inches and about 0.265 inches between the stator and rotor. More torque is produced for a given current density with the smaller gap. The efficiency is slightly greater for the smaller gap since the current is smaller.

As demonstrated, the embodiments thus described address the problems presented in the art. The cheaper impeller as described comprises a magnetic coupling improved by increasing the magnetic field density. Higher torque density is produced by optimizing the impeller magnet by way of material, shape, and back iron, individually or in combination. The rare earth magnets can be replaced by less expensive and environmentally friendly non-rare earth materials, such as Alnico and Ferrite, for example. In addition, the large and oversized drive assembly used prior now can run a much smaller impeller. Further, the moving parts on the drive side, near the user have been repositioned to provide a safer device overall.

Additional technical and commercial advantages are provided with the more reliable system that includes the axial flux stator; the axial flux stator has a smaller drive, no moving parts, and reduced magnetic force during bag installation. While cost and availability of the magnets is an advantage with improving magnet shape and material, the efficiency of the magnetic coupling that increase torque is very useful for further intensification of the bioreactor, various mixing systems, and overall efficiency.

In use, for example, microbial fermentations utilize more agitation for sufficient mixing, gas mass transfer and heat transfer at the reactor wall. An improved device of the invention including the axial flux stator improves user experience due to a less complex design. Not only is the design more compact than a drive with permanent magnets, but the installation and removal of the bag is improved as there are no permanent magnetic forces that have to be overcome. Moving parts are avoided with consequences on machinery directive requirements, sealing and ingress protection to avoid prior standard design that utilized a lever mechanism to separate the drive from the impeller such that the bag can be pulled out of the reactor bottom end piece.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

The invention claimed is:

1. A system to be utilized as bioreactor mixer, the system comprising:
   a rotating drive;
   a fixed shaft;
   an impeller capable of rotating around the fixed shaft;
   a first set of magnets in a first array format positioned at a drive end adjacent the rotating drive and a second set of magnets in a second array format positioned at the impeller; and
   at least one plate including the first set of magnets positioned thereon such that the first set of magnets are positioned in a concentric geometric configuration and individually shaped with a wider outside dimension that narrows toward a center of the concentric geometric configuration;
   wherein the second set of magnets are arranged adjacent one another to augment a magnetic field on one side of the second array while cancelling the magnetic field to zero on an opposite side of the second array to achieve a spatially rotating pattern of magnetization.

2. The system of claim 1, further comprising an external vessel into which at least a portion of the bioreactor mixer is placed.

3. The system of claim 1, wherein the first set of magnets have a slot formed between each individual magnet in the array format, the slot having a slot pitch.

4. The system of claim 1, wherein the first array format of the first set of magnets has uniformity of slot width and magnet height.

5. The system of claim 1, wherein the first set of magnets and the second set of magnets are comprised of rare Earth materials.

6. The system of claim 5, wherein the rare Earth materials include Neodymium and Samarium-Cobalt, individually or in combination.

7. The system of claim 1, wherein the first set of magnets and the second set of magnets are comprised of non-rare Earth materials.

8. The system of claim 7, wherein the non-rare Earth materials include Alnico and Ferrite, alone or in combination.

* * * * *